United States Patent [19]
Yu et al.

[11] Patent Number: 5,942,250
[45] Date of Patent: *Aug. 24, 1999

[54] COMPOSITIONS AND METHODS FOR ENHANCING THE TOPICAL EFFECTS OF SUNSCREEN AGENTS

[75] Inventors: Ruey J. Yu, Ambler; Eugene J. Van Scott, Abington, both of Pa.

[73] Assignee: Tristrata Technology, Inc., Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/478,524

[22] Filed: Jun. 7, 1995

Related U.S. Application Data

[63] Continuation-in-part of application No. 07/393,749, Aug. 15, 1989, Pat. No. 5,091,171, and a continuation of application No. 08/359,939, Dec. 20, 1994, Pat. No. 5,547,988, which is a continuation of application No. 08/117,559, Sep. 7, 1993, abandoned, which is a continuation of application No. 07/936,863, Aug. 27, 1992, abandoned, which is a continuation of application No. 07/683,437, Apr. 10, 1991, abandoned, which is a continuation-in-part of application No. 07/469,738, Jan. 19, 1990, abandoned, which is a continuation of application No. 06/945,680, Dec. 23, 1986, abandoned.

[51] Int. Cl.$^6$ ........................................... A61K 7/00
[52] U.S. Cl. .......................... 424/481; 424/59; 424/60; 514/557; 514/574; 514/844; 514/847; 514/873; 514/941
[58] Field of Search ................ 514/844, 847, 514/873, 557, 574, 941; 424/401, 59, 60

[56] References Cited

U.S. PATENT DOCUMENTS

| | | |
|---|---|---|
| 1,772,975 | 8/1930 | Wieland .................. 514/557 |
| 2,118,566 | 5/1938 | De Wayne ................. 167/90 |
| 3,227,616 | 1/1966 | Van Wessem et al. ........ 167/91 |
| 3,666,863 | 5/1972 | Swanback ................. 424/316 |
| 3,689,668 | 9/1972 | Piette ..................... 514/532 |
| 3,806,593 | 4/1974 | Swanback et al. ............ 424/28 |
| 3,879,537 | 4/1975 | Van Scott et al. .......... 424/311 |
| 3,920,835 | 11/1975 | Van Scott et al. .......... 514/557 |
| 3,984,566 | 10/1976 | Van Scott et al. .......... 424/283 |
| 3,988,470 | 10/1976 | Van Scott et al. .......... 424/283 |
| 3,991,184 | 11/1976 | Kludas et al. ............. 424/177 |
| 4,021,572 | 5/1977 | Van Scott et al. .......... 424/317 |
| 4,053,630 | 10/1977 | Yu et al. ................. 514/494 |
| 4,105,783 | 8/1978 | Yu et al. ................. 424/283 |
| 4,197,316 | 4/1980 | Yu et al. ................. 424/317 |
| 4,234,599 | 11/1980 | Van Scott et al. .......... 424/279 |
| 4,246,261 | 1/1981 | Van Scott et al. .......... 424/240 |
| 4,287,214 | 9/1981 | Van Scott et al. .......... 424/346 |
| 4,363,815 | 12/1982 | Yu et al. ................. 424/274 |
| 4,380,549 | 4/1983 | Van Scott et al. .......... 424/317 |

(List continued on next page.)

FOREIGN PATENT DOCUMENTS

| | | |
|---|---|---|
| 64399 | 7/1975 | Australia . |
| A 57071/90 | 12/1990 | Australia . |
| 0 007 785 | 2/1980 | European Pat. Off. . |
| 007 785 | 2/1980 | European Pat. Off. . |
| 0 007 070 | 8/1983 | European Pat. Off. . |
| 086 070 | 8/1983 | European Pat. Off. . |
| 0 273 202 A2 | 7/1988 | European Pat. Off. . |
| 0 413 528 A1 | 2/1991 | European Pat. Off. . |
| 413 528 | 2/1991 | European Pat. Off. . |
| 1.439.834 | 4/1966 | France . |
| 2517413 | 11/1975 | Germany . |
| 3540175 | 5/1987 | Germany . |
| 58-8007 | 1/1983 | Japan . |
| 752066 | 4/1975 | South Africa . |

OTHER PUBLICATIONS

Yu et al., Alpha Hydroxyacids: Therapeutic Potentials, The Canadian Journal of Dermatology, vol. 1, No. 5 pp. 109–112, (1989).

Gattefosse, R.M., *Formulary of Perfumes and Cosmetics*, Chemical Publishing Co., Inc., pp. 214–215, (1959).

Bergwein, K., *Kosmetik*, 16:555–557, (1967).

Webster's Ninth New Collegiate Dictionary, Merriam–Webster Inc. (1985) p. 1272.

Derwent Abstract 86–064922[10] (Jan. 23, 1986), Nonogawa, Shuji YG.

Derwent Abstract 85–228562[37] (Feb. 23, 1985), Gerchikov, et al.

(List continued on next page.)

Primary Examiner—Jose' G. Dees
Assistant Examiner—Michael A. Williamson
Attorney, Agent, or Firm—Foley & Lardner

[57] ABSTRACT

Uses of topical compositions comprising a 2-hydroxycarboxylic acid or related compound to alleviate or improve signs of skin, nail and hair changes associated with intrinsic or extrinsic aging are disclosed. 2-Hydroxycarboxylic acids and their related compounds include, for example, 2-hydroxyethanoic acid, 2-hydroxypropanoic acid, 2-methyl 2-hydroxypropanoic acid, 2-phenyl 2-hydroxyethanoic acid, 2-phenyl 2-methyl 2-hydroxyethanoic acid, 2-phenyl 3-hydroxypropanoic acid, 2,2-diphenyl 2-hydroxyethanoic acid, 2-hydroxybutane-1,4-dioicacid, 2,3-hihydroxybutane-1,4-dioic acid, 2-carboxy 2-hydroxypentane-1,5-dioic acid, 2-ketopropanoic acid, methyl 2-ketopropanoate, ethyl 2-ketopropanoate, and gluconolactone. Topical application of compositions comprising 2-hydroxycarboxylic acid and/or related compounds has been found to alleviate or improve skin lines; blotches; blemishes; nodules; wrinkles; pigmented spots; atrophy; precancerous lesions; elastotic changes characterized by leathery, coarse, rough, dry and yellowish skin; and other skin changes associated with intrinsic aging or skin damages caused by extrinsic factors such as sunlight, radiations, air pollution, wind, cold, dampness, heat, chemicals, smoke and cigarette smoking. Topical applications of such compositions have also been found to improve the overall qualities of nail and hair affected by intrinsic aging or damaged by extrinsic factors.

14 Claims, No Drawings

U.S. PATENT DOCUMENTS

| | | | | |
|---|---|---|---|---|
| 4,518,789 | 5/1985 | Yu et al. | ................................. | 560/105 |
| 4,612,331 | 9/1986 | Barrett et al. | ............................ | 514/558 |
| 4,929,722 | 5/1990 | Partain et al. | ............................ | 536/20 |
| 4,983,382 | 1/1991 | Wilmott et al. | ............................ | 424/62 |
| 5,021,451 | 6/1991 | McLane et al. | ........................ | 514/460 |
| 5,091,171 | 2/1992 | Yu et al. | ................................. | 424/642 |
| 5,093,109 | 3/1992 | Mausner | .................................... | 424/63 |
| 5,108,751 | 4/1992 | Hagan et al. | ........................... | 424/401 |
| 5,153,230 | 2/1991 | Jeffery | ...................................... | 514/847 |
| 5,665,776 | 9/1997 | Yu et al. | ................................. | 514/557 |

OTHER PUBLICATIONS

Chemical Abstracts 70:14330q (1967), Durafrourd.

Chemical Abstracts 85:25286r (1976), Hadhary, et al.

Chemical Abstracts 108:210190m (1987).

Dorland's Medical Dictionary, 26th Ed., Saunders, Philadelphia, PA (1981) 647, 696–97.

Neostrata Company Notice (1992).

Merck Index, 10th Ed., Rathway, New Jersey, (1983) p. 768.

Weiss, J.S., M.D., et al., "Topical Tretinoin in the Treatment of Aging Skin" *J. Amer. Acad. of Dermatology*, vol. 19 (1988) pp. 169–175.

Weiss, J.S., M.D., et al., "Topical Tretinoin Improves Photoaged Skin: A Double–blind Vehicle Controlled Study", *J. Amer. Medical Assn.*, vol. 259, No. 4 (1988) pp. 527–532.

Moisturizing & Emolliency Documentary, Unusual Moisturizers and Emollients: Patent Digest for 1966–1977, Cosmetics andToiletries, vol. 93, Apr. 1978, pp. 55–60.

Chemical Abstracts 65864w, Bleehen, S.S., Skin Bleaching Preparations, vol. 88 (1978).

Chemical Abstracts 79710x, Juhlin, L.A., Dermatologically Useful Composition, vol. 84 (1976).

Fredriksson, T. et al., Urea Creams in the Treatment of Dry Skin and Hand Dermatitis, Pharmacology and Therapeutics, pp. 442–444 (1975).

Blair, C., The Action of a Urea–Lactic Acid Ointment in Ichthyosis, *British Journal of Dermatology* vol. 94 pp. 145–153 (1976).

Van Scott et al., Control of Keratinization with α–Hydroxyacids and Related Compounds, *Arch Dermatol* vol. 110 pp. 586–590 (1974).

Grice, K., et al.,Urea and Retinoic Acid in Ichthyosis and Their Effect on Transepidermal Water Loss and Water Holding Capacity of Stratum Corneum, *Acta Dermatovener* vol. 53 pp. 114–118 (1973).

Harry, R.G., The Principles and Practice of Modern Cosmetics, 6th Ed.,Chapters 6 and 39, (1973).

Goldenberg, R.L., et al. Correlation of Skin Feel of Emollients to Their Chemical Structure, *J. Soc. Cosmet. Chem.*, vol. 22 pp. 635–654 (1971).

Sadik, F., O–T–C Products for Corns, Calluses, Warts, *Journal of the American Pharmaceutical Association*, vol. NS10, No. 1, pp. 8–12 (1970).

Osipow, L.I., A Buffering Humectant for Cosmetics, *Drug and Cosmetic Industry*, vol. 88, No. 4, pp. 438–515 (1961).

Stern, E.C., Topical Application of Lactic Acid in the Treatment and Prevention of Certain Disorders of the Skin, *The Urologic and Cutaneous Review*, vol. 50, No. 2, pp. 106–107 (1946).

Darr, D., Topical Vitamin C Protects Skin from Ultraviolet Radiation–Induced Damage, *British Journal of Dermatology*, vol. 127 pp. 247–253 (1992).

Aggarwal, R.R., et al., A Clinical Trial with Cotaryl Cream in Hyperkeratotic Skin Conditions, *Indian J. Dermatol. Venerbol.*, vol. 45, No. 6, pp. 442–444 (1979).

//  5,942,250

COMPOSITIONS AND METHODS FOR ENHANCING THE TOPICAL EFFECTS OF SUNSCREEN AGENTS

CROSS-REFERENCE TO RELATED APPLICATIONS

This application is a continuation of application Ser. No. 08/359,939, filed on Dec. 20, 1994, now U.S. Pat. No. 5,547,988, which is a continuation of Ser. No. 08/117,559, filed Sep. 7, 1993, abandoned, which is a continuation of Ser. No. 07/936,863, filed Aug. 27, 1992, abandoned, which is a continuation of Ser. No. 07/683,437, filed Apr. 10, 1991, abandoned, which is a continuation-in-part of Ser. No. 07/469,738, filed Jan. 19, 1990, abandoned, which is a continuation of Ser. No. 06/945,680, filed Dec. 23, 1986, abandoned. This application is also a continuation-in-part of Ser. No. 07/393,749, filed Aug. 15, 1989 now U.S. Pat. No. 5,091,171.

FIELD OF THE INVENTION

This application relates to topical compositions containing a 2-hydroxycarboxylic acid or a related compound for use in alleviating or improving the dermatological signs of aging, including changes or damage to skin, nail and hair associated with intrinsic aging, as well as changes or damage caused by extrinsic factors such as sunlight, radiations, air pollution, wind, cold, heat, dampness, chemicals, smoke, and cigarette smoking.

BRIEF DESCRIPTION OF THE PRIOR ART

In our U.S. Pat. No. 3,879,537 entitled "Treatment of Ichthyosiform Dermatoses" we described and claimed the use of topical compositions containing an alpha hydroxyacid to alleviate the symptoms of ichthyosis. In our U.S. Pat. No. 3,920,835 entitled "Treatment of Disturbed Keratinization" we described and claimed the use of topical compositions containing an alpha hydroxyacid to alleviate the symptoms of acne. In our U.S. Pat. No. 3,984,566 entitled "Method of Alleviating the Symptoms of Dandruff" we described and claimed the use of topical compositions containing an alpha hydroxyacid to improve the symptoms of dandruff.

In our U.S. Pat. No. 4,105,783 entitled "Therapeutic Treatment of Dry Skin"; U.S. Pat. No. 4,197,316 entitled "Treatment of Dry Skin"; and U.S. Pat. No. 4,380,549 entitled "Topical Treatment of Dry Skin"; we described and claimed the use of topical compositions containing an alpha hydroxyacid to alleviate or improve the symptoms of dry skin. In our U.S. Pat. No. 4,234,599 entitled "Treatment of Skin Keratoses with Alpha Hydroxyacids and Related Compounds", we described and claimed the use of topical compositions containing an alpha hydroxyacid or the related compound to alleviate the symptoms of actinic or nonactinic skin keratoses. In our U.S. Pat. No. 4,363,815 entitled "Alpha Hydroxyacids, Alpha Ketoacids and Their Use in Treating Skin Conditions", we described and claimed the use of topical compositions containing certain alpha hydroxyacids or the related compounds to improve skin conditions characterized by inflammation or disturbed keratinization.

In a report entitled "Topical Tretinoin for Photoaged Skin" by Albert M. Kligman, Gary L. Grove, Ryoji Hirose and James J. Leyden published in J. American Academy of Dermatology Vol.15, pages 836–859, 886–887, 1986, daily topical application of 0.05% tretinoin (also known as all-trans retinoic acid) in a cream has been found to improve photodamaged skin. In another report entitled "Topical Tretinoin Improves Photoaged Skin: A Double-blind Vehicle-controlled Study" by Jonathan S. Weiss, Charles N. Ellis, John T. Headington, Theresa Tincoff, Ted A. Hamilton and John J. Voorhees published in J American Medical Association Vol. 259 pages 527–532, 1988, daily topical application of 0.1% tretinoin as compared to vehicle alone application for 16 weeks has been shown to improve photoaged skin. One side-effect has been a dermatitis encountered by 92% of the patients participating in this study. The dermatitis was characterized by a patchy erythema, localized swelling, dry skin, and mild scaling. Patients complained about burning, tingling, or pruritus. In yet another report entitled "Topical Tretinoin in the Treatment of Aging Skin" by Jonathan S. Weiss, Charles N. Ellis, John T. Headington and John J. Voorhees published in J. American Academy of Dermatology Vol.19, pages 169–175, 1988, topical application of 0.1% tretinoin cream for 8 to 12 months has been found to improve clinical signs of aging skin. The side effects have been burning sensation in the eyes and mild skin irritations.

Parent application Ser. No. 07/469,738 described in addition to the main subject certain compositions containing hydroxycarboxylic acids and the related ketocarboxylic acids for topical treatment of wrinkles and skin changes associated with aging. The related application of Ser. No. 07/393,749 described in addition to the main subject a topical treatment to alleviate or remedy warts, nail infections, age spots, wrinkles and aging related skin changes with a composition containing certain alpha hydroxyacids or the related compounds. We have now discovered that 2-hydroxycarboxylic acids and related compounds have much broader utilization than previously disclosed.

SUMMARY OF THE INVENTION

Accordingly, it is an object of this invention to provide methods and compositions which can alleviate signs of skin, nail and hair changes associated with intrinsic and/or extrinsic aging.

We have now discovered that 2-hydroxycarboxylic acids and related compounds have unusual qualities as well as broader utilities which have not been disclosed in the prior art. Topical applications of compositions containing a 2-hydroxycarboxylic acid or a related compound have been found to improve cosmetic as well as clinical signs of changes in skin, nails and hair associated with intrinsic aging, or the damages caused by extrinsic factors such as sunlight, radiations, air pollution, wind, cold, dampness, heat, chemicals, smoke, and cigarette smoking. The signs of skin changes associated with intrinsic aging and the skin damages caused by extrinsic factors include thinning of skin; deepening of skin lines; wrinkles; blemishes; blotches; nodules; atrophy; pigmented spots; precancerous lesions; elastotic changes characterized by leathery, coarse, rough, dry and yellowish skin; and telangiectatic skin. The signs of nails and hair changes associated with intrinsic aging and the damages caused by extrinsic factors include thinning, fragility, splitting, lack of luster, uneven surface, and loss of flexibility and elasticity. 2-Hydroxycarboxylic acids and their related compounds which are useful for topical treatment of skin, nail and hair changes associated with intrinsic and/or extrinsic aging include, inter alia, 2-hydroxyethanoic acid, 2-hydroxypropanoic acid, 2-methyl 2-hydroxypropanoic acid, 2-phenyl 2-hydroxyehtanoic acid, 2-phenyl 2-methyl 2-hydroxyethanoic acid, 2-phenyl 3-hydroxypropanoic acid, 2,2-diphenyl 2-hydroxyethanoic acid, 2-hydroxybutane-1,4-dioic acid, 2,3-dihydroxybutane-1,4-dioic acid, 2-carboxy 2-hydroxypentane-1,5-dioic acid, 2-ketopropanoic acid, methyl 2-ketopropanoate, ethyl 2-ketopropanoate, and gluconolactone.

Additional objects and advantages of the invention will be set forth in part in the description that follows, and in part will be obvious from the description, or may be learned by practice of the invention. The objects and the advantages of this invention may be realized and obtained by means of the compositions and methods particularly pointed out in the appended claims.

DETAILED DESCRIPTION OF THE PREFERRED EMBODIMENTS

Cutaneous aging is associated with intrinsic factors with or without the additional factors of extrinsic origin. The intrinsic aging is due to internal physiologic functions and is an inherent aging process of living beings, which has not been reversible nor preventable. However, a modification, improvement or alleviation of the signs associated with cutaneous aging is now possible in accordance with this invention. Extrinsic aging, on the other hand, is due to external factors such as sunlight, radiations, air pollution, wind, cold, dampness, heat, chemicals, smoke, and cigarette smoking. A modification, improvement or alleviation of the signs associated with the extrinsic aging of skin, nails and hair is also now possible in accordance with this invention. Moreover, in some cases, it may be possible to eradicate such signs of intrinsic and extrinsic aging.

In the protected areas of skin such as abdomen and upper arm, the signs of skin aging which are caused by intrinsic factors include progressive thinning of skin, deepening of skin lines, wrinkles, dry and lusterless skin surface, loss of skin elasticity and recoilability. In the sun exposed areas of skin such as face and hands, the signs of intrinsic aging plus those of photoaging include deep wrinkles; marked loss of elasticity and recoilability; coarse, uneven and dry skin; blemished and leathery skin; loss of skin lubricating substances; and increased numbers of blotches, nodules and pigmented spots.

Histologically, the qualities and quantities of elastin and collagen tissues are changed. Normal elastin in tissues is replaced by abnormal elastin characterized as solar elastosis, and the normal collagen fibers are decreased.

The signs of nail and hair changes associated with intrinsic aging and the damages caused by extrinsic factors include thinning of hair and nail plate; lack of lubricants and luster, and uneven surface of hair and nails; fragility and splitting of hair and nails; and reduction of flexibility, resiliency, and elasticity of hair and nails.

The conventional management for signs of aging skin has been the use of cosmetics as well as medical procedures such as phenol, trichloroacetic acid, and other chemical peels, and plastic surgery etc. Such medical procedures are costly and risky with serious side effects, and the treatments alter only the cosmetic appearance of the skin, without any significant modifications of the underlying aging process.

As mentioned in the previous section, recent medical reports claimed the use of topical compositions containing tretinoin to improve clinical signs of skin aging associated with intrinsic factors as well as the skin damages caused by sunlight. However, use of tretinoin has been associated with certain adverse skin reactions such as dry skin, scaling, burning, tingling, itching, erythema, skin dermatitis, localized swelling, and induction of photosensitivity.

We have now discovered that use of topical compositions containing 2-hydroxycarboxylic acid or related compounds are therapeutically effective in modification or eradication of clinical signs of cutaneous aging with minimal if any side effects or discomfort.

For convenience, the 2-hydroxycarboxylic acids and related compounds which may be used in accordance with this invention may be classified into three groups, namely (1) 2-hydroxycarboxylic acids, (2) 2-ketocarboxylic acids and esters thereof, and (3) other related compounds. The related compounds may include hydroxycarboxylic acids with the hydroxyl group at any position other than position 2, for example position 3, position 4 or position 5, as well as cyclic hydroxycarboxylic acids (e.g., ascorbic acid and quinic acid), and also may include ketocarboxylic acids and asters thereof. Preferred related compounds include 3-hydroxycarboxylic acids, and 2-ketocarboxylic acids and esters thereof.

Group 1

The first group comprises organic carboxylic acids in which one hydroxy group is attached to the 2 position carbon atom of the acid. The generic structure of such 2-hydroxycarboxylic acids may be represented as follows:

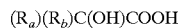

Where $R_a$ and $R_b$ may be the same or different and are independently selected from H, F, Cl, Br, alkyl, aralkyl or aryl group of saturated or unsaturated, isomeric or non-isomeric, straight or branched chain or cyclic form, having 1 to 29 carbon atoms, and in addition $R_a$ and $R_b$ may carry OH, CHO, COOH and alkoxy group having 1 to 9 carbon atoms. 2-Hydroxycarboxylic acids may be present as a free acid or lactone form, or in a salt form with an organic base or an inorganic alkali. 2-Hydroxycarboxylic acids may exist as stereoiscmers as D, L, and DL forms when $R_a$ and $R_b$ are not identical.

Typical alkyl, aralkyl and aryl groups for $R_a$, and $R_b$ include methyl, ethyl, propyl, isopropyl, butyl, pentyl, octyl, decyl, dodecyl, hexadecyl, benzyl, and phenyl, etc. 2-Hydroxycarboxylic acids of the first group may be further divided into subgroups comprising (1) alkyl hydroxycarboxylic acids, (2) aralkyl and aryl hydroxycarboxylic acids, (3) polyhydroxy-carboxylic acids, and (4) hydroxy-polycarboxylic acids. The following are representative 2-hydroxycarboxylic acids in each subgroup.

(1) Alkyl Hydroxycarboxylic Acids 1. 2-Hydroxyethanoic acid (Glycolic acid, hydroxyacetic acid)

(H)(H)C(OH)COOH 2. 2-Hydroxypropanoic acid (Lactic acid)

$(CH_3)(H)C(OH)COOH$ 3. 2-Methyl 2-hydroxypropanoic acid (Methyllactic acid)

$(CH_3)(CH_3)C(OH)COOH$ 4. 2-Hydroxybutanoic acid $(C_2H_5)(H)C(OH)COOH$ 5. 2-Hydroxypentanoic acid $(C_3H_7)(H)C(OH)COOH$ 6. 2-Hydroxyhexanoic acid $(C_4H_9)(H)C(OH)COOH$ 7. 2-Hydroxyheptanoic acid $(C_5H_{11})(H)C(OH)COOH$ 8. 2-Hydroxyoctanoic acid $(C_6H_{13})(H)C(OH)COOH$ 9. 2-Hydroxynonanoic acid $(C_7H_{15})(H)C(OH)COOH$ 10. 2-Hydroxydecanoic acid $(C_8H_{17})(H)C(OH)COOH$ 11. 2-Hydroxyundecanoic acid
   ($C_9H_{19}$)(H)C(OH)COOH
12. 2-Hydroxydodecanoic acid (Alpha hydroxylauric acid)
   ($C_{10}H_{21}$)(H)C(OH)COOH
13. 2-Hydroxytetradecanoic acid (Alpha hydroxymyristic acid)
   ($C_{12}H_{25}$)(H)C(OH)COOH
14. 2-Hydroxyhexadecanoic acid (Alpha hydroxypalmitic acid)
   ($C_{14}H_{29}$)(H)C(OH)COOH
15. 2-Hydroxyoctadecanoic acid (Alpha hydroxystearic acid)
   ($C_{16}H_{33}$)(H)C(OH)COOH
16. 2-Hydroxyeicosanoic acid (Alpha hydroxyarachidonic acid)
   ($C_{18}H_{37}$)(H)C(OH)COOH
17. 2-Hydroxytetraeicosanoic acid (Cerebronic acid)
   ($C_{22}H_{45}$)(H)C(OH)COOH
18. 2-Hydroxytetraeicosenoic acid (Alpha hydroxynervonic acid)
   ($C_{22}H_{43}$)(H)C(OH)COOH (2) Aralkyl And Aryl 2-Hydroxycarboxylic Acids
1. 2-Phenyl 2-hydroxyethanoic acid (Mandelic acid)
   ($C_6H_5$)(H)C(OH)COOH
2. 2,2-Diphenyl 2-hydroxyethanoic acid (Benzilic acid)
   ($C_6H_5$)($C_6H_5$)C(OH)COOH
3. 3-Phenyl 2-hydroxypropanoic acid (Phenyllactic acid)
   ($C_6H_5CH_2$)(H)C(OH)COOH
4. 2-Phenyl 2-methyl 2-hydroxyethanoic acid (Atrolactic acid)
   ($C_6H_5$)($CH_3$)C(OH)COOH
5. 2-(4'-Hydroxyphenyl) 2-hydroxyethanoic acid (4-Hydroxymandelic acid)
   (HO—$C_6H_4$)(H)C(OH)COOH
6. 2-(4'-Chlorophenyl) 2-hydroxyethanoic acid (4-Chloromandelic acid)
   (Cl—$C_6H_4$)(H)C(OH)COOH
7. 2-(3'-Hydroxy-4'-methoxyphenyl) 2-hydroxyethanoic acid (3-Hydroxy-4-methoxymandelic acid)
   (HO—,$CH_3O$—$C_6H_3$)(H)C(OH)COOH
8. 2-(4'-Hydroxy-3'-methoxyphenyl) 2-hydroxyethanoic acid (4-Hydroxy-3-methoxymandelic acid)
   (HO—,$CH_3O$—$C_6H_3$)(H)C(OH)COOH
9. 3-(2'-Hydroxyphenyl) 2-hydroxypropanoic acid [3-(2'Hydroxyphenyl) lactic acid]
   (HO—$C_6H_4$—$CH_2$)(H)C(OH)COOH
10. 3-(4'-Hydroxyphenyl) 2-hydroxypropanoic acid [3-(4'-Hydroxyphenyl) lactic acid]
    (HO—$C_6H_4$—$CH_2$)(H)C(OH)COOH
11. 2-(3',4'-Dihydroxyphenyl) 2-hydroxyethanoic acid (3,4-Dihydroxyinandelic acid)
    (HO—,HO—$C_6H_3$)(H)C(OH)COOH (3) Polyhydroxy-carboxylic Acids
1. 2,3-Dihydroxypropanoic acid (Glyceric acid)
   ($HOCH_2$)(H)C(OH)COOH
2. 2,3,4-Trihydroxybutanoic acid (Isomers; erythronic acid, threonic acid)
   ($HOCH_2$ HOCH)(H)C(OH)COOH
3. 2,3,4,5-Tetrahydroxypentanoic acid (Isomers; ribonic acid, arabinoic acid, xylonic acid, lyxonic acid)
   ($HOCH_2$ HOCH HOCH)(H)C(OH)COOH
4. 2,3,4,5,6-Pentahydroxyhexanoic acid (Isomers; allonic acid, altronic acid, gluconic acid, mannoic acid, gulonic acid, idonic acid, galactonic acid, talonic acid)
   ($HOCH_2$ HOCH HOCH HOCH)(H)C(OH)COOH
5. 2,3,4,5,6,7-Hexahydroxyheptanoic acid (Isomers; glucoheptonic acid, galactoheptonic acid etc.)
   ($HOCH_2$ HOCH HOCH HOCH HOCH)(H)C(OH)COOH (4) Hydroxy-polycarboxylic Acids
1. 2-Hydroxypropane-1,3-dioic acid (Tartronic acid)
   (HOOC)(H)C(OH)COOH
2. 2-Hydroxybutane-1,4-dioic acid (Malic acid)
   (HOOC $CH_2$)(H)C(OH)COOH
3. 2,3-Dihydroxybutane-1,4-dioic acid (Tartaric acid)
   (HOOC HOCH)(H)C(OH)COOH
4. 2-Hydroxy-2-carboxypentane-1,5-dioic acid (Citric acid)
   (HOOC $CH_2$)$_2$C(OH)COOH
5. 2,3,4,5-Tetrahydroxyhexane-1,6-dioic acid (Isomers; saccharic acid, mucic acid etc.)
   HOOC(CHOH)$_4$ COOH The 2-hydroxycarboxylic acids may be present in forms other than the acid, such as, for example, salts or lactones. Typical lactone forms which may be used in accordance with this invention include, for example, gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

Group 2

The second group, which comprises compounds related to the 2-hydroxycarboxylic acids, includes organic carboxylic acids in which one keto group is attached to position 2 carbon atom of the acid. The generic structure of such 2-ketoacids may be represented as follows:

($R_c$)COCOO($R_d$)

wherein $R_c$ and $R_d$ can be the same or different and are each selected from H, alkyl, aralkyl or aryl group of saturated or unsaturated, isomeric or non-isomeric, straight or branched chain or cyclic form, having 1 to 29 carbon atoms, and in addition $R_c$ may carry F, Cl, Br, I, OH, CHO, COOH and alkoxy group having 1 to 9 carbon atoms. The alpha ketoacids may be present as a free acid or an ester form, or in a salt form with an organic base or an inorganic alkali. The typical alkyl, aralkyl and aryl groups for $R_c$ and $R_d$ include methyl, ethyl, propyl, 2-propyl, butyl, pentyl, hexyl, octyl, dodecyl, hexadecyl, benzyl and phenyl.

In contrast to 2-hydroxycarboxylic acids of the first group compounds, the ester form of 2-ketocarboxylic acids has been found to be therapeutically effective for signs and symptoms of cutaneous aging including intrinsic and extrinsic aging. For example, while methyl 2-hydroxypropanoate and ethyl 2-hydroxypropanoate have minimal effects, methyl 2-ketopropanoate and ethyl 2-ketopropanoate are therapeutically very effective. The real mechanism for such difference is not known. We have speculated that the ester form of the 2-ketocarboxylic acid is chemically and/or biochemically very reactive, and a free 2-ketocarboxylic acid may be released in the skin after penetration through the stratum corneum of the skin. The representative 2-ketocarboxylic acids and their esters of the second group are listed below:

1. 2-Ketoethanoic acid (Glyoxylic acid)
   (H)COCOOH
2. Methyl 2-ketoethanoate
   (H)COCOO$CH_3$
3. 2-Ketopropanoic acid (Pyruvic acid)
   $CH_3$COCOOH 4. Methyl 2-ketopropanoate (Methyl pyruvate)
   $CH_3COCOOCH_3$
5. Ethyl 2-ketopropanoate (Ethyl pyruvate)
   $CH_3COCOOC_2H_5$
6. Propyl 2-ketopropanoate (Propyl pyruvate)
   $CH_3COCOOC_3H_7$
7. 2-Phenyl-2-ketoethanoic acid (Benzoylformic acid)
   $C_6H_5COCOOH$
8. Methyl 2-phenyl-2-ketoethanoate (Methyl benzoylformate)
   $C_6H_5COCOOCH_3$
9. Ethyl 2-phenyl-2-ketoethanoate (Ethyl benzoylformate)
   $C_6H_5COCOOC_2H_5$
10. 3-Phenyl-2-ketopropanoic acid (Phenylpyruvic acid)
    $C_6H_5CH_2COCOOH$
11. Methyl 3-phenyl-2-ketopropanoate (Methyl phenylpyruvate)
    $C_6H_5CH_2COCOOCH_3$
12. Ethyl 3-phenyl-2-ketopropanoate (Ethyl phenylpyruvate)
    $C_6H_5CH_2COCOOC_2H_5$
13. 2-ketobutanoic acid
    $C_2H_5COCOOH$
14. 2-Ketopentanoic acid
    $C_3H_7COCOOH$
15. 2-Ketohexanoic acid
    $C_4H_9COCOOH$
16. 2-Ketoheptanoic acid
    $C_5H_{11}COCOOH$
17. 2-Ketooctanoic acid
    $C_6H_{13}COCOOH$
18. 2-Ketododecanoic acid
    $C_{10}H_{21}COCOOH$
19. Methyl 2-ketooctanoate
    $C_6H_{14}COCOOCH_3$ Group 3

The third group, which also comprises related compounds, includes, inter alia, hydroxycarboxylic acids where the hydroxy is at a position other than position 2, and cyclic hydroxycarboxylic acids which are useful for topical application to improve signs of aging skin and the cutaneous appendages. The members of this group, which are more conveniently identified by name than by generic structures, include ascorbic acid, quinic acid, isocitric acid, tropic acid (2-phenyl 3-hydroxypropanoic acid), trethocanic acid, 3-chlorolactic acid, citramalic acid, agaricic acid, aleuritic acid, pantoic acid, lactobionic acid and hexulosonic acid.

Amplifying Bioactivities of Cosmetic and Pharmaceutical Agents

The compositions of present invention may contain one or more 2-hydroxycarboxylic acids or related compounds to magnify the therapeutic effect of an unrelated cosmetic or pharmaceutical agent. At least one compound selected from the group consisted of 2-hydroxycarboxylic acids and related compounds may be incorporated into a composition containing a cosmetic or pharmaceutical agent for topical treatment to improve or alleviate signs of skin, nails or hair changes associated with intrinsic aging or the damages caused by extrinsic factors. It has been found that such incorporation have resulted in magnified therapeutic efficacies which are not simply additive effects.

Most pharmaceutical drugs produce their therapeutic effects by first interacting with their receptors in the target tissues. Many drug receptors are functional macromolecules such as enzymes, cell membrane components or certain components of cells. The binding affinity or interacting property of a drug toward its specific receptor molecule is intimately governed by the chemical structure of the drug. Since most pharmaceutical agents are chemically different from 2-hydroxycarboxylic acids and related compounds, the respective receptor molecules should be different and so are the pharmacologic actions and the therapeutic effects. Under such conditions if 2-hydroxycarboxylic acid or a related compound is incorporated into a composition containing a pharmaceutical agent, one of the following two consequences may arise:

(a) No enhancement or any substantial changes in either effect. In this case, the overall clinical effect would be a mixing effect, i.e. the effect due to the pharmaceutical agent alone mixed with the effect due to the 2-hydroxycarboxylic acid or the related compound alone. Also in this case, the interaction between the pharmaceutical agent and its receptor molecule is not affected nor interfered by the presence of 2-hydroxycarboxylic acid or the related compound. Nor does 2-hydroxycarboxylic acid or the related compound assist in or enhance the binding affinity or the interaction of the pharmaceutical agent toward its receptor molecule. The clinical results from such combination composition would be just the mixing effects, and are predictable.

(b) Amplified therapeutic action or substantial loss of therapeutic action in either effect. In this case, the interaction between the pharmaceutical agent and its receptor molecule is affected either positively or negatively by the presence of 2-hydroxycarboxylic acid or the related compound. From the point of positive effect, 2-hydroxycarboxylic acid or the related compound may produce an amplified effect by either increasing the affinity of the receptor molecule toward the pharmaceutical agent; acting as a better and more efficient coenzyme or as an activator by disrupting barriers and removing obstacles for better binding of the agent toward its receptor molecule; for example, enzyme activation by removal of natural inhibitors. In all these cases the overall clinical results would be due to magnified therapeutic effects which are not predictable from either effect alone.

From the point of negative effect, a 2-hydroxycarboxylic acid or a related compound might interfere with or decrease the binding affinity of the pharmaceutical agent toward its receptor molecule; i.e. acting as an inhibitor. In such case, the overall clinical results should be due to a substantial diminishment or completely loss of therapeutic effects, which is also unpredictable from either effect alone.

We have found that, in most cases, therapeutic effects of cosmetic and pharmaceutical agents are amplified when a 2-hydroxycarboxylic acid or a related compound is incorporated into the composition, i.e., consequence (b) above is observed.

The cosmetic and pharmaceutical agents which may be actuated by 2-hydroxycarboxylic acids or related compounds include those that improve or eradicate age spots, keratoses and wrinkles by different mechanism of action; antimicrobial and antiacne agents; antipruritic and antixerotic agents; antiinflammatory agents; sunscreen and antiphotosensitive agents; nail and hair conditioners, cleansers, care and treatment agents; wart removers; skin lightening agents; depigmenting agents; local anesthetics and analgesics; corticosteroids; retinoids; vitamins; hormones; and antimetabolites.

Some examples of cosmetic and pharmaceutical agents include acyclovir, amphotericins, chlorhexidine, clotrimazole, ketoconazole, miconazole, metronidazole, minocycline, nystatin, neomycin, kanamycin, phenytoin, octyl dimethyl PABA, octyl methoxycinnamate, PABA and other esters, octyl salicylate, oxybenzone, dioxybenzone, tocopherol, tocopheryl acetate, selenium sulfide, zinc pyrithione, soluble elastin, diphenhydramine, pramoxine, lidocaine, procaine, erythromycin, tetracycline, clindamycin, hydroquinone and its monomethyl and benzyl ethers, naproxen, ibuprofen, cromolyn, retinoic acid, retinol, retinyl palmitate, retinyl acetate, coal tar, griseofulvin, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, minoxidil, dipyridamole, diphenylhydantoin, benzoyl peroxide and 5-fluorouracil.

Specific Compositions For Skin And Skin Appendages

While 2-hydroxycarboxylic acids and related compounds are therapeutically effective for topical treatment to improve or alleviate signs of skin, nail or hair changes associated with intrinsic aging and/or photoaging, certain compounds of the instant invention are more potent than others. In selecting a particular compound of the present invention two factors, namely (a) potency and (b) concentration have to be considered. If rapid results are preferred in certain cases, most potent compounds with highest and safe concentrations may be used. Under such conditions the treatment time is substantially shortened with good to excellent clinical results. Generally, such treatment has to be carried out under supervision by a dermatologist or trained professional in the office, medical center, skin care center, or beauty salon etc. Such procedure or treatment may include micro and semimicro peels, epidermolysis or superficial peel, and dermolysis or deeper peel.

Examples of more potent 2-hydroxycarboxylic acids and related compounds to be formulated in specific compositions include 2-hydroxyethanoic acid, 2-hydroxypropanoic acid, 2-methyl 2-hydroxypropanoic acid, 2-phenyl 2-hydroxyethanoic acid, 2,2-diphenyl 2-hydroxyethanoic acid, 2-phenyl 2-methyl 2-hydroxyethanoic acid, 2-phenyl 3-hydroxypropanoic acid, 2-ketopropanoic acid, methyl 2-ketopropanoate and ethyl 2-ketopropanoate. The concentration of 2-hydroxycarboxylic acid or the related compound used in such specific composition may range from an intermediate to a full strength, therefore the dispensing and the application require special handling and procedures.

If the 2-hydroxycarboxylic acid or the related compound at full strength (usually 85–100%) is a liquid form at room temperature such as 2-hydroxypropanoic acid, 2-ketopropanoic acid, methyl 2-ketopropanoate and ethyl 2-ketopropanoate, the liquid compound with or without a gelling agent is directly dispensed as 0.5 to 1 ml aliquots in small vials.

If the 2-hydroxycarboxylic acid or the related compound at full strength is a crystalline or solid form at room temperature such as 2-hydroxyethanoic acid, 2-methyl 2-hydroxypropanoic acid, 2-phenyl 2-hydroxyethanoic acid, 2,2-diphenyl 2-hydroxyethanoic acid and 2-phenyl 3-hydroxypropanoic acid, the crystalline or solid compound is first dissolved in a minimal amount of vehicle or vehicle system prepared from water, ethanol, propylene glycol and/or butylene glycol with or without a gelling agent. For example, 2-hydroxyethanoic acid 70 g is dissolved in water 30 ml, and the 70% strength solution thus obtained is dispensed as 0.5 to 1 ml aliquots in small vials. If a gelling agent is used 0.1 to 2% of hydroxyethyl cellulose, methyl cellulose, hydroxypropyl cellulose, chitosan, carbomer, or polyquaternium-10 may be incorporated into the above solution.

To formulate an intermediate strength (usually 20–50%), 2-hydroxycarboxylic acid or the related compound either a liquid or solid form at room temperature is first dissolved in a vehicle or vehicle system prepared from water, acetone, ethanol, propylene glycol and/or butylene glycol. For example, 2-hydroxyethanoic acid or 2-ketopropanoic acid 30 g is dissolved in ethanol 56 g and propylene glycol 14 g, and the 30% strength solution thus obtained is dispensed as 7 to 14 ml aliquots in dropper bottles.

General Preparation of Compositions

Most compositions of the instant invention may be formulated as solution, gel, lotion, cream, ointment, or other pharmaceutically acceptable form. To prepare a composition in solution form for general use, at least one 2-hydroxycarboxylic acid or related compound is dissolved in a solution prepared from ethanol, water, propylene glycol, butylene glycol, acetone or other pharmaceutically acceptable vehicle. The concentration of the 2-hydroxycarboxylic acid or related compound may range from 0.1 to 100 percent, the preferred concentration ranges being from about 2 to about 25 percent for home use, with higher ranges, e.g., from about 70 to about 100 percent being acceptable for office use where professional supervision is provided. Thus, such concentrations can also range from about 25 to about 50 percent and from about 50 to about 70 percent, with the proviso that concentrations of about 25 percent or more generally requiring profession supervision.

In the preparation of a composition in lotion, cream or ointment form, at least one of 2-hydroxycarboxylic acids or related compounds is initially dissolved in a solvent such as water, ethanol, butylene glycol, and/or propylene glycol. The solution thus prepared is then mixed in a conventional manner with commonly available cream or ointment base such as hydrophilic ointment or petrolatum. The concentrations of 2-hydroxycarboxylic acids or related compounds used in the compositions are the same as described above.

Thin gel compositions are specifically useful for topical application to hair and face. A typical gel composition of the instant invention is formulated by dissolving at least one of 2-hydroxycarboxylic acids or related compounds in a vehicle prepared from ethanol, water, butylene glycol, and/or propylene glycol. A gelling agent such as xanthan gum, polyquaternium-10, methyl cellulose, ethyl cellulose, hydroxyethylcellulose, hydroxypropylcellulose, chitosan, hydroxypropylmethylcellulose, ammoniated glycyrrhizinate or carbomer is then added to the solution with agitation. The preferred concentration of the gelling agent may range from 0.1 to 2 percent by weight of the total composition.

To prepare an actuated composition, a cosmetic or pharmaceutical agent is incorporated into any one of the above formulations by dissolving or mixing the agent into the composition.

The following are illustrative examples of formulations and compositions according to this invention. Although the examples utilize only selected compounds and formulations, it should be understood that the following examples are illustrative and not limited. Therefore, any of the aforementioned 2-hydroxycarboxylic acids and related compounds may be substituted according to the teachings of this invention in the following examples.

EXAMPLE 1

A typical solution composition containing 2-hydroxycarboxylic acid or the related compound may be formulated as follows. 2-Hydroxyethanoic acid (glycolic acid) crystals 7 g is dissolved in water 50 ml and propylene glycol 15 ml. Ethanol is added to the solution until the total volume is 100 ml. The composition thus prepared contains 7% w/v 2-hydroxyethanoic acid.

EXAMPLE 2

A typical gel composition containing 2-hydroxycarboxylic acid or the related compound may be formulated as follows.

2-Hydroxypropanoic acid (DL-lactic acid) USP grade 5 g is dissolved in water 60 ml and butylene glycol 10 ml, and chitosan or polyquaternium-10 0.3 g is added with stirring. Ethanol is added to the mixture until the volume is 100 ml. The mixture is stirred until a uniform gel is obtained. The thin gel thus obtained contains 5% 2-hydroxypropanoic acid.

EXAMPLE 3

A typical oil-in-water emulsion containing 2-hydroxycarboxylic acid or the related compound may be formulated as follows.

2-Methyl 2-hydroxypropanoic acid (methyllactic acid) crystals 10 g is dissolved in water 20 ml and concentrated ammonium hydroxide 2 ml is added to the solution. The solution is mixed with enough hydrophilic ointment USP to make a total weight of 100 g. The cream thus formulated contains 10% 2-methyl 2-hydroxypropanoic acid.

EXAMPLE 4

A typical water-in-oil emulsion containing 2-hydroxycarboxylic acid or the related compound may be formulated as follows.

Gluconolactone 7 g is dissolved in water 12 ml and concentrated ammonium hydroxide 0.5 ml is added to the solution. The solution is mixed with enough water-in-oil emulsion to make a total weight of 100 g. The water non-washable cream thus formulated contains 7% gluconolactone.

EXAMPLE 5

A typical ointment containing 2-hydroxycarboxylic acid or the related compound may be formulated as follows.

2-Phenyl 2-hydroxyethanoic acid (mandelic acid) crystals 10 g is dissoLved in 10 ml ethanol, and the solution thus formed is mixed with mineral oil 35 g and enough white petroleum to make a total weight of 100 g. The ointment thus formulated contains 10% 2-phenyl 2-hydroxyethanoic acid.

EXAMPLE 6

A specific preparation containing a full strength or a high concentration of 2-hydroxycarboxylic acid or the related compound may be formulated and dispensed as follows.

If 2-hydroxycarboxylic acid or the related compound at full strength is a liquid form at room temperature such as 2-hydroxypropanoic acid, 2-ketopropanoic acid, methyl 2-ketopropanoate and ethyl 2-ketopropanoate, the compound is directly dispensed as 0.5 to 1 ml aliquots in small vials. If the compound is a crystalline or solid form, such as 2-hydroxyethanoic acid, 2-methyl 2-hydroxypropanoic acid, 2-phenyl 2-hydroxyethanoic acid, 2-phenyl 3-hydroxypropanoic acid, 2-phenyl 2-methyl 2-hydroxyethanoic acid and 2,2-diphenyl 2-hydroxyethanoic acid, the compound is first dissolved in minimal amount of an appropriate vehicle system selected from water, ethanol, propylene glycol and butylene glycol with or without a gelling agent. For example, 2-hydroxyethanoic acid 70 g is dissolved in water 30 ml, and 70% strength 2-hydroxyethanoic acid with or without addition of 0.5% chitosan or polyquaternium-10 is dispensed as 1 to 5 ml aliquots in small vials.

EXAMPLE 7

A typical preparation containing an intermediate strength of 2-hydroxycarboxylic acid or the related compound may be formulated as follows.

Malic acid, tartaric acid or citric acid 35 g is dissolved in water 60 ml and propylene glycol 5 ml. The 35% strength solution thus prepared is dispensed as 5 to 10 ml aliquots in dropper bottles.

EXAMPLE 8

A composition containing 2-hydroxycarboxylic acid or the related compound to magnify the therapeutic effect of a cosmetic or pharmaceutical agent for wrinkles and other signs of skin aging may be formulated as follows.

Ethyl 2-ketopropanoate (ethyl pyruvate) 2 g and all-trans retinoic acid 0.02 g are dissolved in a vehicle system prepared from ethanol 50 ml, water 28 ml and propylene glycol 20 ml. The composition thus formulated contains retinoic acid 0.02% and ethyl 2-ketopropanoate 2%.

EXAMPLE 9

A composition containing 2-hydroxycarboxylic acid or the related compound to amplify the therapeutic effect of a dermatologic agent for blemishes, pigmented spots and wrinkles may be formulated as follows.

2-Hydroxyethanoic acid 8 g, hydroquinone 2 g and sodium metabisulfite 0.4 g are dissolved in a vehicle prepared from ethanol 30 ml, water 45 ml and propylene glycol 15 ml. Chitosan or polyquaternium-10 0.3 g is added to the solution with stirring. The mixture is stirred until a uniform gel is obtained. The thin gel thus obtained contains hydroquinone 2% and 2-hydroxyethanoic acid 8%.

EXAMPLE 10

A typical cleansing and soothing composition containing 2-hydroxycarboxylic acid or the related compound to enhance the therapeutic effect of a dermatologic agent for initial treatment of hair or skin changes associated with aging may be formulated as follows.

2,2-Diphenyl 2-hydroxyethanoic acid (benzilic acid) 2 g and chlorhexidine 0.3 g are dissolved in a vehicle system prepared from ethanol 30 ml, water 58 ml and butylene glycol 10 ml. The solution thus formulated contains chlorhexidine 0.3% and 2,2-diphenyl 2-hydroxyethanoic acid 2%.

EXAMPLE 11

A typical lotion containing 2-hydroxycarboxylic acid or the related compound to substantiate and magnify the sunscreen effect of a dermatologic agent may be formulated as follows.

2-Hydroxyethanoic acid 3 g and concentrated ammonium hydroxide 0.75 ml are dissolved in water 7 ml, and the solution thus obtained is mixed with 85 g of an oil-in-water emulsion which contains octyl methoxycinnamate 5 g. The actuated sunscreen lotion thus formulated contains 5% sunscreen agent and 3% 2-hydroxyethanoic acid.

TEST RESULTS

(1) Biologic and Pharmacologic Actions

The skin may be classified into two major parts; dermis and epidermis. The dermis contains blood vessels, nerves, collagen, elastin etc, and fibroblast cells in the dermis are responsible for the biosynthesis of collagen and elastin. The epidermis contains nerves but no collagen, elastin, nor blood vessels.

The epidermis is further divided into two distinct zones; malpighian layer and horny layer. The malpighian layer, a living tissue, is further divided into basal, spinous, and granular layers. The horny layer, a dead tissue, is also called stratum corneum. In the natural process, basal cells in the basal layer move outward through the spinous and granular layers to become dead cells called corneocytes, in the stratum corneum. The stratum corneum consists of approximately 14 layers of corneocytes. In normal skin it takes about 14 days for the basal cells to move from the basal layer to the end of the granular layer and to become corneocytes, and another 14 days to reach the outermost layer of the stratum corneum. This process of forming corneocytes is called keratinization, and stratum corneum, nail, and hair are the natural products produced by such process. The stratum corneum is the skin tissue that one feels when touching the skin. Usually, it takes about 28 days for cells of the basal layer to move outward to the surface in the course of making new skin.

We have found that compositions containing low concentrations of 2-hydroxycarboxylic acid or the related compound, when applied topically to the skin, diminish corneocyte cohesion in the stratum corneum. This effect predominantly occurs among corneocyte cells at inner levels of the stratum corneum, i.e. near the junction to the granular layer, and there is no effect among corneocyte cells at outer layers in the stratum corneum. Therefore, 2-hydroxycarboxylic acids and related compounds are not typical keratolytics such as strong acids, strong alkalis, thiols, urea and lithium salts which cause disaggregation of corneocyte cells in the outer layers of the stratum corneum.

We have also discovered that compositions containing intermediate to high concentrations of 2-hydroxycarboxylic acid or the related compound, when topically applied to the skin, cause profound beneficial effects in the dermis as well as the epidermis of the skin. The skin becomes thicker and plump as measured clinically by caliper and micrometer techniques. Histometric techniques using microscopic analysis of tissue biopsy specimens confirm that new and more collagen and elastic fibers have been biosynthesized in the dermis.

The biologic and pharmacologic actions of 2-hydroxycarboxylic acid or the related compound suggest that topical application of the composition should improve or alleviate signs of skin, nail, and hair changes associated with intrinsic and/or extrinsic aging.

(2) Therapeutic Effects

In order to determine whether compositions containing 2-hydroxycarboxylic acid or the related compound were therapeutically effective for topical application to improve or alleviate signs of skin, nail, and hair changes associated with intrinsic and/or extrinsic aging, a total of more than 120 volunteers and patients participated in these studies. Intrinsic aging is due to internal physiologic process, different from the damage caused by an external factor such as sunlight. The body areas showing predominantly intrinsic aging are in the protected regions of the skin such as abdomen, buttock, and upper arm. The signs of intrinsic aging include thinning of skin, deepening of natural skin lines, fine wrinkles, dry and lusterless skin surface, loss of skin elasticity and recoilability. Therefore, for intrinsic aging test compositions were topically applied to the skin of upper arms and/or abdomen.

The extrinsic aging is a progressive damage caused by environmental factors such as sunlight, radiations, air pollution, wind, cold, dampness, heat, chemicals, smoke, and/or smoking. The body areas predominantly involved are in the exposed regions of the skin such as face, scalp with thin or no hair, neck, forearms, and the back of hands. The signs of extrinsic aging in these skin areas are in most cases a combination of intrinsic aging and extrinsic aging unless it involves a very young person. The signs of both intrinsic and extrinsic aging include fine and deep wrinkles, loss of elasticity and recoilability, coarse and very dry skin, blemished and leathery skin, loss of skin lubricants, and increased numbers of age spots, blotches, nodules and pigmented spots. In such cases test compositions were topically applied to face, forearms, and the back of hands.

The composition containing a weak to intermediate concentration of 2-hydroxycarboxylic acid or the related compound was topically applied to the skin by a patient or a participating subject at home, as a home treatment. The composition containing a high concentration or a full strength of 2-hydroxycarboxylic acid or the related compound was topically applied to the involved skin of a patient, such as the face, by a dermatologist or a trained health professional as an office procedure or treatment. For rapid therapeutic results, both home and office treatments were adopted in many cases.

(a) Home Treatment

In order to determine whether the composition containing a 2-hydroxycarboxylic acid or related compound was therapeutically effective for topical application to alleviate or improve signs of skin changes associated with intrinsic and extrinsic aging on the face or the back of hands, both patients and volunteer subjects were included in the study. The compositions containing 5 to 30%, and preferably between 8 to 20%, of a 2-hydroxycarboxylic acid or related compound were formulated with optimal bioavailability of the active ingredient according to the examples. The participants were instructed to apply the compositions twice daily on the face and the back of hands for intervals of 2 to 12 months. All participants were instructed to avoid sun exposure, and to use a sunscreen product with a sun protection factor of 15 or greater if exposure to sunlight was unavoidable.

Photographs of each side of the face, and the back of hands were taken at the beginning of the study and repeated at one to three-month intervals. The participants were asked not to wear facial makeup nor to apply any products on the back of hands at the time of the visit, except for eye shadow if desired. Standardized photographic conditions were used: the same light source at two feet from the face aimed at a locus on the frontal aspect of each cheek, end also at two feet from the back of hands. Photographs were taken with the camera aimed perpendicular to the cheek or the back of hands.

After 2 months of home treatment all of a group of 35 participants showed substantial improvement of the face and the back of hands. The skin was smoother, glossy, and softer. Blotches, blemishes, and age spots on the face were also decreased in number or were lighter in color in a group of 30 out of 35 closely monitored participants. After 6 to 9 months of continued home treatment, skin lines and fine wrinkles on the face either disappeared or were diminished in 24 out of this group of 35 participants. Great numbers of age spots and blemishes on the face and the back of hands also continued to disappear or become much less conspicuous. The skin appeared and felt smooth, soft, and glossy. Coarser wrinkles were substantially reduced after 18 months of continued home treatment.

(b) Office Treatment

Specific compositions containing a high concentration to a full strength of a 2-hydroxycarboxylic acid or related compound were used in most cases as an office procedure or treatment. The composition containing 2-hydroxyethanoic acid, 2-hydroxypropanoic acid, 2-ketopropanoic acid, 2-methyl 2-hydroxypropanoic acid, 2phenyl 2-hydroxyethanoic acid, or 2,2-diphenyl 2-hydroxyethanoic acid at concentrations of 50% or higher was prepared according to the examples.

The composition was topically applied to the skin and gently massaged in with the fingers or a cotton ball by a dermatologist or a trained health professional who wore rubber gloves. After 1 to a few minutes, depending on the strength used and the skin sensitivity of the subject, the skin was gently rinsed with water.

Such office treatment was repeated every 2 to 3 weeks. Photographs of the skin so treated were taken at the beginning of the study and repeated at one to three-month intervals as described in the previous section.

After one to two office treatments, all 32 patients in this particular study showed distinct improvement of the face and other areas treated, such as the forearms, the back and the back of hands. The original coarse, rough, and dry skin had improved markedly, and the skin was smooth, glossy, and soft. The number of blotches, blemishes, brownish spots, and age spots decreased significantly after 3 to 5 office treatments. Facial skin lines and fine wrinkles improved or disappeared in 25 out of this group of 32 patients after 8 to 12 office treatments.

(c) Office Treatment Plus Home Treatment

If rapid therapeutic results are desired, home treatment may be combined with the office treatment. After each office treatment, the patient would topically apply twice daily a composition containing a low to intermediate concentration of a 2-hydroxycarboxylic acid or related compound on the face and the back of hands.

After one office treatment plus twice daily home treatment, all 28 patients of this study showed marked improvement on the texture of treated skin. The rough, coarse, and dry skin disappeared, and the skin was smooth, glossy, and soft after one month. Blotches, blemishes, nodules, age spots, pigmented spots, skin lines, and fine wrinkles improved or disappeared, 3 to 5 months after the office treatment plus the home treatment. Deep wrinkles started to improve visibly as measured by photographic means after 5 to 10 months of sustained office treatments and continued home treatments.

Most patients showed marked improvement of deep wrinkles after 12 to 18 months of combined office and home treatments.

(d) Epidermolysis and Dermolysis

While the office procedure described in the previous section causes a micro or semimicro peeling of the skin, procedures which cause epidermolysis and dermolysis result in superficial and deeper peeling of the skin. When a composition containing a high concentration or a full strength of a 2-hydroxycarboxylic acid or related compound such as 70% 2-hydroxyethanoic acid, 85% 2-hydroxypropanoic acid, and 100% 2-ketopropanoic acid is topically applied to a photodamaged skin, epidermolysis will occur if the time of contact with the skin is long enough.

The epidermolysis is clinically beneficial for topical treatment of acne, age spots, keratoses, pigmented spots, skin lines, blemishes, wrinkles and other signs of skin changes associated with intrinsic and extrinsic aging.

In general, epidermolysis of skin occurs faster on the face than on the upper back or the back of hands, and faster on skin of younger people than of older people. and usually faster in women than men. The clinical sign of epidermolysis is blanching of the skin, a sign that signals the threshold between superficial peeling and deeper peeling. When blanching of the skin is first seen the skin is immediately rinsed with water to prevent a deeper peeling of the skin.

In dermatologic practice dermolysis or deep peeling has been induced for the treatment of blemished skin or aging skin by using peeling agents such as trichloroacetic acid and phenol. These peeling agents are very caustic to the skin and are also toxic. serious side effects including death have been reported. A 2-hydroxycarboxylic acid or related compound can be safely used as a micro, semimicro, superficial or deep peeling agent for topical treatment of dermatologic disorders including skin changes associated with intrinsic aging or skin damages caused by extrinsic aging such as photoaging.

The face of a patient to be so treated was initially wiped with 70% ethanol, and the eyes were covered with wet cotton balls. A full strength (100%) 2-ketopropanoic acid, or an aqueous solution containing 70% 2-hydroxyethanoic acid or 85% 2-hydroxypropanoic acid was uniformly applied to the skin using a cotton ball. The patient usually feel a transient burning sensation. Erythema usually appeared after less than a minute up to a few minutes depending on the skin type, age, sex etc. The skin was rinsed with water after blanching of the skin occurred or intense erythema persisted.

A total of 23 patients participated in the epidermolysis study. Most participants also daily used emollient lotions or creams containing weak concentrations of a 2-hydroxycarboxylic acid or related compound. All the participants showed marked improvement of skin lines, blemishes and fine wrinkles after 2 months.

(3) Amplified Bioactivities

We have discovered that when a 2-hydroxycarboxylic acid or related compound is incorporated into a composition containing a dermatologic agent, the pharmacologic actions and the therapeutic effects are unexpectedly amplified in most cases. For example, a 2-hydroxycarboxylic acid or related compound magnifies the therapeutic effects of hydroquinone, 5-fluorouracil, chlorhexidine, clotrimazole, miconazole, tetracycline, retinoic acid etc. Compositions containing 2-hydroxycarboxylic acid or the related compound and a dermatological or other pharmaceutical agent were formulated according to the examples.

Each participating patient received two compositions; i.e. with or without the incorporation of a 2-hydroxycarboxylic acid or related compound. The patients were instructed to apply topically one medication on one side of the body such as on the back of the left hand and the other medication on the other side of the body such as on the back of the right hand. Specific instructions were given to the patients to apply the medications twice daily to the involved areas or lesions of blemishes, age spots, melasmas, lentigines, skin lines, wrinkles, or precancerous actinic keratoses. Clinical improvements were discernible after a few weeks to a few months of topical application. The sides treated with amplified compositions were substantially better than the sides treated with the medications which did not contain any 2-hydroxycarboxylic acid or the related compound.

(4) Hair and Nail Treatments

Compositions containing a 2-hydroxycarboxylic acid or related compound at low concentrations, preferably from 1 to 4%, for hair care and treatment were formulated according to the examples. A solution or thin gel form thus formulated was topically applied to the hair after shampoo. The same treatment was repeated 3 to 4 times weekly. After a few weeks to a few months of such treatment, the signs of hair changes associated with intrinsic aging and the damages caused by photoaging started to improve substantially. The hair first appeared smooth and shiny. The hair became softer to the touch and feel. After a few months of such treatment, hair increased its elasticity and flexibility.

Compositions containing 2-hydroxycarboxylic acid or the related compound at intermediate concentrations, preferably from 8 to 20%, for nail care and treatment were formulated according to the examples. A solution or thin gel form thus prepared was topically applied twice daily to edges, surface and base of affected nail plates. After a few months of such treatment, the signs of nail changes associated with intrinsic and extrinsic aging started to improve noticeably. The nail looked glossy and felt smooth on the surface. The flexibility and elasticity of the nail after the treatment also increased. Brittleness diminished and the occurrence of terminal nail splitting became rare.

It will be apparent to those skilled in the art that various modifications and variations can be made to the compositions of matter and methods of this invention. Thus, it is intended that the present invention covers such modifications and variations.

What is claimed is:

1. A method for enhancing the cosmetic and therapeutic effects of a composition comprising a sunscreen agent, comprising combining with said composition an enhancing amount of at least one 2-hydroxycarboxylic acid or related compound selected from the group consisting of glycolic acid, lactic acid, mandelic acid, benzilic acid, citric acid, pyruvic acid, ethyl puruvate, methyl pyruvate, malic acid, tartaric acid, gluconolactone, ribonolactone, galactonolactone, lactobionic acid, quinic acid, isocitric acid, tropic acid, trethocanic acid, phenyllactic acid, glucoheptonic acid, saccharic acid, mucic acid, atrolactic acid, citramalic acid, agaricic acid, aleuritic acid, cerebronic acid, 2-hydroxynervonic acid, 4-hydroxymandelic acid, glyceric acid, 2,3,4-trihydroxybutanoic acid, 2,3,4,5-tetrahydroxypentanoic acid, 2,3,4,5,6-pentahydroxyhexanoic acid, 2,3,4,5,6,7-hexahydroxyheptanoic acid and isomers and stereoisomers thereof;

wherein said 2-hydroxycarboxylic acid or related compound may be in free acid, lactone, salt, or ester form.

2. A method according to claim 1 wherein said 2-hydroxycarboxylic acid or related compound is glycolic acid.

3. A method according to claim 1 wherein said 2-hydroxycarboxylic acid or related compound is lactic acid.

4. A method according to claim 1 wherein said 2-hydroxycarboxylic acid or related compound is citric acid.

5. A method according to claim 1 wherein said 2-hydroxycarboxylic acid or related compound is tartaric acid.

6. A method according to claim 1 wherein said 2-hydroxycarboxylic acid or related compound is gluconolactone.

7. A method according to claim 1 wherein said 2-hydroxycarboxylic acid or related compound is lactobionic acid or a salt thereof.

8. A topical composition comprising a sunscreen agent and an enhancing amount of at least one 2-hydroxycarboxylic acid or related compound selected from the group consisting of glycolic acid, lactic acid, mandelic acid, benzillic acid, citric acid, pyruvic acid, ethyl puruvate, methyl pyruvate, malic acid, tartaric acid, gluconolactone, ribonolactone and galactonolactone.

9. A topical composition according to claim 8 wherein said 2-hydroxycarboxylic acid or related compound is glycolic acid.

10. A topical composition according to claim 8 wherein said 2-hydroxycarboxylic acid or related compound is lactic acid.

11. A topical composition according to claim 8 wherein said 2-hydroxycarboxylic acid or related compound is citric acid.

12. A topical composition according to claim 8 wherein said 2-hydroxycarboxylic acid or related compound is tartaric acid.

13. A topical composition according to claim 8 wherein said 2-hydroxycarboxylic acid or related compound is gluconolactone.

14. A topical composition according to claim 8 wherein said 2-hydroxycarboxylic acid or related compound is lactobionic acid or a salt thereof.

* * * * *